United States Patent [19]

Komatsu et al.

[11] Patent Number: 5,334,789
[45] Date of Patent: Aug. 2, 1994

[54] OXYCHLORINATION CATALYST PROCESS FOR PREPARING THE CATALYST AND METHOD OF OXYCHLORINATION WITH USE OF THE CATALYST

[75] Inventors: Masashi Komatsu, Ibaraki; Michio Yamamoto, Otsu; Masaru Ishino, Ichihara; Gohfu Suzukamo, Suita, all of Japan

[73] Assignee: Sumitomo Chemical Company, Limited, Osaka, Japan

[21] Appl. No.: 83,502

[22] Filed: Jun. 30, 1993

[30] Foreign Application Priority Data

Jun. 30, 1992 [JP] Japan .................. 4-172465

[51] Int. Cl.$^5$ .................................. C07C 17/156
[52] U.S. Cl. .................. 570/203; 570/224; 570/182; 570/189
[58] Field of Search .......... 570/224, 203, 182, 189

[56] References Cited

U.S. PATENT DOCUMENTS

| | | | |
|---|---|---|---|
| 3,354,234 | 11/1967 | Hayden et al. | 570/224 |
| 3,670,034 | 6/1972 | Robinson | 568/774 |
| 4,058,574 | 11/1977 | Daumas | 570/245 |
| 4,300,005 | 11/1981 | Li | 570/224 |

FOREIGN PATENT DOCUMENTS

| | | |
|---|---|---|
| 0238700 | 9/1987 | European Pat. Off. . |
| 1300930 | 11/1969 | Fed. Rep. of Germany . |
| 1157584 | 7/1969 | United Kingdom . |

*Primary Examiner*—Johann Richter
*Assistant Examiner*—Michael B. Hydorn
*Attorney, Agent, or Firm*—Cushman, Darby & Cushman

[57] ABSTRACT

Disclosed are an oxychlorination catalyst comprising a carrier material, and a palladium compound, a copper compound and a vanadium compound which are supported on the carrier material; an oxychlorination catalyst comprising a carrier material, and a palladium compound, a copper compound, a vanadium compound and an alkaline earth metal compound which are supported on the carrier material; processes for preparing these catalysts; and a method for oxychlorination of an olefin or an aromatic hydrocarbon using one of these catalysts.

20 Claims, No Drawings

OXYCHLORINATION CATALYST PROCESS FOR PREPARING THE CATALYST AND METHOD OF OXYCHLORINATION WITH USE OF THE CATALYST

FIELD OF THE INVENTION

The present invention relates to a catalyst for oxychlorination, and more particularly to an oxychlorination catalyst comprising a palladium compound, a copper compound, a vanadium compound and optionally an alkaline earth metal compound, each of which is supported on a carrier material.

PRIOR ART

Oxychlorination is known as a method of introducing chlorine into an olefin, an aromatic hydrocarbon or the like using hydrogen chloride and oxygen. It is also known that a catalyst comprising a palladium compound supported on a carrier is used in oxychlorination.

For example, known are a method for preparing allyl chloride from propylene using a catalyst comprising palladium chloride supported on active carbon (Japanese Unexamined Patent Publication (Kokai) No.1504/1974), and a method of oxychlorination wherein a catalyst comprising palladium chloride, copper chloride and potassium chloride each supported on alumina is used ( German Patent No. 1,300,930 ).

However, these methods are not fully satisfactory from a commercial viewpoint in respect of the catalytic activity, selectivity and life of the catalyst.

SUMMARY OF THE INVENTION

The present inventors carried out extensive research to develop efficient catalysts for oxychlorination and found that a catalyst comprising a palladium compound, a copper compound and a vanadium compound as supported on a carrier material exhibits a high catalytic activity and that the catalyst shows a pronouncedly improved selectivity when the catalyst further contains an alkaline earth metal compound supported on the carrier material.

According to the present invention, there is provided an oxychlorination catalyst comprising (i) a carrier material, and (ii) a palladium compound, a copper compound and a vanadium compound.

The catalyst may further contain an alkaline earth metal compound as supported on the carrier material. Thus, the present invention also provides an oxychlorination catalyst comprising (i) a carrier material, and (ii) a palladium compound, a copper compound, a vanadium compound and an alkaline earth metal compound.

The present invention further provides processes for preparing these catalysts as well as a method for oxychlorination of an olefin or an aromatic hydrocarbon using the catalyst.

DETAILED DESCRIPTION OF THE INVENTION

The present invention will be described below in more detail.

Useful carrier materials are, for example, oxides, carbides and the like. Specific examples of carrier materials include, for example, $SiO_2$, $Al_2O_3$, $SiO_2$-$Al_2O_3$, $TiO_2$, $MgO$, $CaO$, $La_2O_3$, $CeO_2$, $SiO_2$-$TiO_2$, $SiC$, carbon, zeolite and clay minerals. Among these, $SiO_2$, $Al_2O_3$ and $TiO_2$ are preferable among which $TiO_2$ is more preferable. It is preferable that the carrier material has a specific surface area of about 20-350 $m^2/g$ as determined by the BET method.

Examples of useful palladium compound are salts, oxides and complexes of bivalent palladium and so on.

Specific examples of palladium compound include, for example, palladium halides such as $PdCl_2$, $PdBr_2$ and $PdI_2$, palladium nitrates such as $Pd(NO_3)_2$, palladium sulfates such as $PdSO_4$, carboxylic acid salts (particularly $C_1$-$C_7$ carboxylic acid salts) of palladium such as $Pd(O_2CCH_3)_2$, $Pd(O_2CC_2H_5)_2$ and $Pd(O_2CC_3H_7)$, oxides of palladium such as $PdO$, hydroxides of palladium such as $Pd(OH)_2$ and complexes of palladium such as $Pd(NO_2)_2(NH_3)_2$, $[Pd(NH_3)_4]Cl_2$,$PdCl_2(NH_3)_2$, $[Pd(NH_3)_4](NO_3)_2$, $Pd(CN)_2$, $K_2[Pd(CN)_4]$, $Pd(CN)_2(NH_3)_2$, $PdCl_2(CH_3CN)_2$, $PdCl_2(PhCN)_2$, $PdCl_2$ (1,5-cyclooctadiene ), $Pd(CH_3COCHCOCH_3)_2$, $PdCl_2[(Ph)_3P]_2$, $(NH_4)_2[PdCl_6]$, $(NH_4)_2[PdCl_4]$, $K_2[PdCl_6]$, $K_2[PdCl_4]$, $K_2[Pd(NO_2)_4]$, $Na_2[PdCl_4]$, $Na_2[Pd(NO_2)_4]$ and $Pd[(Ph)_3P]_4$. These compounds can be used singly, or at least two of them can be used in combination. Preferably used are water-soluble compounds such as halides, nitric acid salts, sulfuric acid salts, carboxylic acid salts, ammine complexes, cyanide complexes, double salts of these, and the like. More preferable are $Pd(O_2CCH_3)_2$, $Pd(O_2CC_2H_5)_2$, $Pd(O_2CC_3H_7)_2$, $PdCl_2$, etc.

Examples of useful copper compound are salts, oxides and complexes of monovalent or bivalent copper.

Specific examples of copper compound are salts of copper such as $CuCl$, $CuCl_2$, $CuBr$, $CuBr_2$, $CuI_2$, $Cu(NO_3)_2$, $CuSO_4$, $Cu_2(CN)_2$, $Cu(CN)_2$, $Cu(OH)_2$, $Cu_2P_2O_7$, $CuCO_3$ and $2CuCO_3 \cdot Cu(OH)_2$, oxides of copper such as $CuO$ and $Cu_2O$ and complexes of copper such as $Cu(O_2CCH_3)_2$, $Cu(CH_3COCHCOCH_3)_2$, $[Cu(NH_3)_6]Cl_2$ and $[Cu(NH_3)_5]Cl_2$, among which $CuCl_2$ and $Cu(NO_3)_2$ are preferably used. These compounds can be used singly, or at least two of them can be used in combination.

Examples of useful vanadium compounds are salts and oxides of vanadium and the like.

Specific examples of vanadium compound include, for example, $V_2O_3$, $VO_2$, $V_2O_5$, $NH_4VO_3$, $Na_3VO_4$, $Na_4V_2O_7$, $VOCl_3$, $VCl_4$, $VCl_5$ and $VOSO_4$ among which $V_2O_5$ is preferable.

Examples of useful alkaline earth metal compound are halides, nitric acid salts, sulfuric acid salts and carboxylic acid salts of magnesium, calcium, strontium and barium.

Specific examples of alkaline earth metal compound include, for example, $MgCl_2$, $MgBr_2$, $MgI_2$, $Mg(NO_3)_2$, $MgSO_4$, $Mg(O_2CCH_3)_2$, $Mg(O_2CC_2H_5)_2$, $Mg(O_2CC_6H_5)_2$, $Mg(O_2CH)_2$, magnesium phthalate, magnesium citrate, magnesium glycolate, $CaCl_2$, $CaBr_2$, $CaI_2$, $Ca(NO_3)_2$, $CaSO_4$, $Ca(O_2CCH_3)_2$, $Ca(O_2CC_2H_5)_2$, $Ca(O_2CC_6H_5)$ $Ca(O_2CH)_2$, calcium phthalate, calcium citrate, calcium glycolate $SrCl_2$, $SrBr_2$, $SrI_2$, $Sr(NO_3)_2$, $SrSO_4$, $Sr(O_2CH)_2$, $BaCl_2$, $BaBr_2$, $BaI_2$, $Ba(NO_3)_2$, $BaSO_4$ and $Ba(O_2CH)_2$, among which magnesium salts are preferred and organic acid salts (particularly $C_1$-$C_8$ organic acid salts) of magnesium are more preferred.

The presence of such alkaline earth metal compound supported on the carrier material results in inhibited production of carbon dioxide as a by-product and in enhanced selectivity with respect to the contemplated chlorinated product.

In the oxychlorination catalyst of the present invention, the amounts of components, based on the carrier material, are as follows. The palladium compound is used in an amount of about 0.01 to about 20% by weight, preferably about 0.1 to about 10% by weight, calculated as palladium. The copper compound is used in an amount of about 0.05 to about 40% by weight, preferably about 0.5 to about 20% by weight, calculated as copper. The vanadium compound is used in an amount of about 0.05 to about 40% by weight, preferably about 0.5 to about 20% by weight, calculated as vanadium.

When the oxychlorination catalyst further comprises an alkaline earth metal compound, the alkaline earth metal compound is usually used, based on the carrier material, in an amount of up to about 40% by weight, preferably 1 to about 20% by weight, calculated as alkaline earth metal.

The oxychlorination catalyst of the present invention is usually prepared by causing the carrier material to support thereon the catalyst metal compounds, for example, as follows.

The palladium compound, the copper compound, the vanadium compound and optionally the alkaline earth metal compound are mixed together in the presence of a solvent in the proportions that correspond to the above-mentioned amounts. Examples of useful solvents are water, alcohols such as methanol, ethanol, 1-propanol, 2-propanol or ethylene glycol, ethers such as ethylene glycol methyl ether, trimethyleneglycol methyl ether, tetrahydrofuran or dioxane, ketones such as acetone, methyl ethyl ketone, diethyl ketone or methyl isobutyl ketone, and the like, among which water is usually used. The mixing is conducted usually at a temperature below the boiling point of the solvent used.

The mixture may be a uniform solution, or a slurry. It is possible to add an amine complexing agent such as ammonia, ethylene diamine or the like or an acid such as hydrochloric acid in order to accelerate the dissolution of the compounds.

Subsequently a carrier material is added to the mixture, followed by thorough stirring. Then the solvent is evaporated off, giving the desired oxychlorination catalyst. The evaporation may be conducted under atmospheric pressure or under reduced pressure at a temperature ranging from room temperature to about 200° C.

The foregoing procedure is one of the preferred embodiments of the process for preparing the oxychlorination catalyst according to the present invention. The order and manner of mixing the metal compounds and the carrier material are not particularly limited but may be suitably selected.

Thus, the present invention provides a process for preparing an oxychlorination catalyst comprising the steps of mixing a carrier material, a palladium compound, a copper compound, a vanadium compound and if desired an alkaline earth metal compound in the presence of a solvent, and evaporating the solvent.

The obtained catalyst can be used as it is, or in the form of a molded product, or after calcination in an oxygen-containing gas or in a nitrogen atmosphere at about 200° to about 700° C. for about 1 to about 10 hours. The oxygen-containing gas to be used may be, for example, oxygen or air, optionally as diluted with an inert gas such as nitrogen, carbon dioxide or the like.

If desired, the catalyst may also be used as diluted with a conventional diluent such as silicon carbide, alumina, titania, silica, zircon or glass beads, or may be used after the addition of alumina sol, carbon or the like for the improvement of the mechanical strength.

The catalyst thus obtained for use in the invention can be used either in a fixed bed or in a fluidized bed.

The oxychlorination of olefins or aromatic hydrocarbons can be conducted using the catalyst of the invention under the condition conventionally employed. The oxychlorination of olefins or aromatic hydrocarbons using the catalyst of the invention may be conducted in a liquid phase, but is usually conducted in a gas phase. Advantageously, the starting compounds, i.e., an olefin or an aromatic hydrocarbon, hydrogen chloride and oxygen and if desired an inert gas are passed over the solid catalyst. Especially, it is preferable to pass a starting gas mixture containing these reactants and optionally an inert gas through a reaction tube filled with a catalyst.

Examples of olefins to be used in the oxychlorination are lower olefins, particularly $C_2$-$C_6$ olefins, which may be substituted with at least one halogen atoms, particularly with 1-3 halogen atoms, such as ethylene, propylene, butene, pentene, hexene, vinyl chloride and so on. Examples of aromatic hydrocarbons to be used in the oxychlorination are benzene or naphthalene, each of which may have 1 to 7, preferably 1 to 5, substituents selected from the group consisting of a $C_1$-$C_4$ alkyl group and a halogen atom, such as benzene, toluene, xylene, chlorobenzene and the like. Preferred among them are ethylene, propylene, benzene and the like, from which vinyl chloride, allyl chloride, chlorobenzene and the like can be efficiently produced, respectively.

The mole ratio of olefin or aromatic hydrocarbon: hydrogen chloride: oxygen is 1:0.1–10:0.05–5, preferably 1:0.5–2:0.25–2. The hydrogen chloride may be pure hydrogen chloride, or may be used in admixture with nitrogen, carbon dioxide or like inert gases, methane or like hydrocarbon, water and so on. The oxygen may be pure oxygen, or may be used in admixture with an inert gas and therefore air may be used.

If desired, an inert gas such as nitrogen or carbon dioxide may be supplied as diluent gas to the reaction system. It is preferable to use the inert gas in an amount of up to 50 times (by volume), preferably up to 10 times (by volume), the amount of olefin or aromatic hydrocarbon.

The reaction is carried out at a temperature of about 150° to about 400° C., preferably about 200° to about 300° C. at a pressure ranging from atmospheric pressure to about 10 Kg/cm$^2$ G.

The starting gas (i.e., a mixture of olefin or aromatic hydrocarbon, hydrogen chloride, oxygen and if desired an inert gas) is supplied at a space velocity (GHSV) of about 100 to about 100,000 h$^{-1}$, preferably about 500 to about 10,000 h$^{-1}$.

The resulting reaction mixture is then cooled, washed with water and if desired purified by a conventional method such as distillation, thereby giving the desired oxychlorination product.

When the oxychlorination is continued for a prolonged period of time, the catalytic activity and/or selectivity may be lowered. In this case, the catalyst can be regenerated to recover the catalytic activity and/or selectivity by introducing an oxygen-containing gas and calcinating the catalyst. The oxygen-containing gases to be used may be, for example, oxygen or air, optionally as diluted with an inert gas such as nitrogen, carbon dioxide or the like.

The calcination temperature for regeneration is about 150° to about 750° C., preferably about 250° to about 600° C. The pressure ranges from atmospheric pressure to about 10 Kg/cm$^2$ G. The oxygen-containing gas is fed at a space velocity (GHSV) of about 100 to about 100,000 h$^{-1}$, preferably about 500 to about 10,000 h$^{-1}$. The calcination time is about 0.5 to about 10 hours, preferably about 1 to about 5 hours, although variable depending on the calcination temperature.

The oxychlorination catalyst of the invention exhibits high catalytic activity and high selectivity, and can introduce chlorine into olefins, aromatic hydrocarbons or the like with high efficiency.

Furthermore, since the catalyst of the invention has a prolonged life and can be regenerated with ease, the catalyst of the invention is advantageous also from a commercial viewpoint.

The present invention will be described below in more detail with reference to the following examples and comparative examples. However, the invention is not limited to the examples.

EXAMPLE 1

A 5 ml quantity of 0.5N hydrochloric acid was placed into a 50 ml flask, and 0.083 g of palladium chloride and 0.87 g of copper (II) chloride dihydrate were added. The mixture was heated to 70° C. to provide a solution.

The solution was cooled to room temperature. Divanadium pentoxide (0.42 g), 5 g of SiO$_2$ (product of Nikki Chemical Co., Ltd., "E8G1") and 10 g of distilled water were added and the mixture was evaporated to remove solvent at 70° C. under a reduced pressure of 20 to 30 mmHg. The obtained solid was dried at 110° C.

The obtained powder was cooled to room temperature and press-molded with a tablet machine. The molded product was crushed and passed through a sieve, giving particles (Catalyst-1) with a particle size adjusted to 48 to 60 mesh.

A reaction tube made of pyrex glass (10 mm in inner diameter, 450 mm in length) were filled with 0.5 g (0.7 ml) of Catalyst-1. The tube was placed into an electric furnace (35 mm in diameter, 400 mm in length) equipped with a thermostat. Oxygen and nitrogen were supplied to the tube in amounts of 8 and 32 mmol/h, respectively with use of mass flow control valves while gradually elevating the furnace temperature to 500° C. The catalyst was calcined at the same temperature for 1 hour and cooled to 220° C.

Then propylene, hydrogen chloride, oxygen and nitrogen were fed to the reaction tube in amounts of 8, 8, 4 and 16 mmol/h, respectively with use of mass flow control valves. The reaction was conducted while maintaining the furnace temperature at 220° C. The reaction mixture was subjected to analysis by gas chromatography. Table 1 shows the reaction results measured 8 hours after the initiation of the reaction.

The conversion, AC (allyl chloride) selectivity, and CO$_2$ produced (%) were calculated by the following equations:

Conversion (%)=[1−(amount of unreacted propylene (mol)+amount of produced isopropyl chloride (mol))/amount of fed propylene (mol)]× 100 =

AC selectivity (%)

[amount of produced AC (mol)/(amount of reacted propylene (mol)−amount of produced isopropyl chloride (mol))]× 100

CO$_2$ produced (%)=[(amount of produced CO$_2$ (mol)-×⅓)/(amount of reacted propylene (mol)−amount of produced isopropyl chloride (mol))]×100

EXAMPLE 2

Catalyst-2 was produced by the same procedure as in Example 1 with the exception of using 5 g of titanium (IV) dioxide (product of Sakai Chemical Industry Co., Ltd. ) in place of SiO$_2$. The reaction was conducted in the same manner as in Example 1 with the exception of using Catalyst-2 ( 0.5 g, 0.5 ml ). Table 1 shows the results.

EXAMPLE 3

Catalyst-3 was produced by the same procedure as in Example 1 with the exception of using 5 g of titanium (IV) dioxide (product of Sakai Chemical Industry Co., Ltd. ) and 0.4 g of magnesium citrate in place of SiO$_2$. The reaction was conducted in the same manner as in Example 1 with the exception of using Catalyst-3 (0.5 g, 0.5 ml). Table 1 shows the results.

COMPARATIVE EXAMPLE 1

Catalyst-4 was produced by the same procedure as in Example 1 except that copper (II) chloride dihydrate and divanadium pentoxide were not used.

The reaction was conducted in the same manner as in Example 1 with the exception of using Catalyst-4 (0.5 g, 0.7 ml). Table 1 shows the results.

COMPARATIVE EXAMPLE 2

Catalyst-5 was produced by the same procedure as in Example 1 except that divanadium pentoxide was not used.

The reaction was conducted in the same manner as in Example 1 with the exception of using Catalyst-5 (0.5 g, 0.7 ml). Table 1 shows the results. The catalyst exhibited the desired level of catalytic activity in the initial stage of the reaction but showed substantially no catalytic activity 8 hours after the initiation of the reaction.

COMPARATIVE EXAMPLE 3

Catalyst-6 was produced by the same procedure as in Example 1 except that copper (II) chloride dihydrate was not used.

The reaction was conducted in the same manner as in Example 1 with the exception of using Catalyst-6 (0.5 g, 0.7 ml). Table 1 shows the results.

TABLE 1

|  | Catalyst | Conversion (%) | AC selectivity (%) | CO$_2$ Produced (%) |
|---|---|---|---|---|
| Ex. 1 | Catalyst-1 | 9.0 | 69.4 | 3.5 |
| Ex. 2 | Catalyst-2 | 22.0 | 71.5 | 13.7 |
| Ex. 3 | Catalyst-3 | 26.2 | 80.4 | 3.2 |
| Comp. Ex. 1 | Catalyst-4 | 7.5 | 0.8 | — |
| Comp. Ex. 2 | Catalyst-5 | 0.0 | — | — |
| Comp. Ex. 3 | Catalyst-6 | 1.0 | 13.8 | — |

EXAMPLE 4

Catalyst-3 (2 g, 2 ml) was placed into the same reaction tube as used in Example 1, and the tube was placed in the same electric furnace as employed in Example 1.

Oxygen and nitrogen were supplied to the reaction tube in amounts of 16 and 64 mmol/h, respectively with use of mass flow control valves while gradually elevating the furnace temperature to 500° C. The catalyst was calcined at the same temperature for 1 hour and cooled to 220° C.

Subsequently propylene, hydrogen chloride, oxygen and nitrogen were supplied in amounts of 16, 16, 8 and 32 mmol/h, respectively with use of mass flow control valves. The reaction was conducted while maintaining the furnace temperature at 245° C.

One hundred hours after the initiation of the reaction, the catalyst was regenerated by supplying oxygen and nitrogen in amounts of 8 and 32 mmol/h, respectively while gradually elevating the furnace temperature to 400° C. Thereafter the catalyst was calcined at the same temperature for 3 hours, and the furnace was cooled to a temperature of 220° C.

Subsequently propylene, hydrogen chloride, oxygen and nitrogen were supplied again in amounts of 16, 16, 8 and 32 mmol/h, respectively. The reaction was conducted while maintaining the furnace temperature at 245° C.

Table 2 below shows the reaction performance data measured 90 and 200 hours after the initiation of the reaction. The catalyst was regenerated every 100 hours, and was subjected to the reaction for a total of 600 hours. The catalyst showed little or no decrease in the catalytic activity and selectivity.

TABLE 2

| Reaction time (h) | Conversion (%) | AC selectivity (%) | $CO_2$ produced (%) |
|---|---|---|---|
| 90 | 31 | 69 | 9 |
| 200 | 33 | 72 | 6 |
| 300 | 30 | 76 | 4 |
| 400 | 19 | 77 | 3 |
| 500 | 21 | 82 | 3 |
| 600 | 21 | 78 | 4 |

EXAMPLE 5

Catalyst-2 (0.5 g, 0.5 ml) was placed into the same reaction tube as used in Example 1, and the tube was placed in the same electric furnace as employed in Example 1. Oxygen and nitrogen were supplied to the reaction tube in amounts of 8 and 32 mmol/h, respectively with use of mass flow control valves while gradually elevating the furnace temperature to 300° C. The catalyst was calcined at the same temperature for 1 hour and cooled to 240° C.

Then benzene was fed in an amount of 8 mmol/h via a microfeeder, and hydrogen chloride, oxygen, and nitrogen were fed in amounts of 8, 4 and 16 mmmol/h, respectively with use of mass flow control valves. The reaction was conducted while maintaining the furnace temperature at 240° C. An analysis by gas chromatography was conducted with respect to the reaction mixture obtained 4 hours after the initiation of the reaction.

The analysis by gas chromatography shows that the conversion of benzene was 52.9% and the selectivity of monochlorobenzene was 79.8%.

We claim:

1. A method for oxychlorination of an olefin or an aromatic hydrocarbon in the presence of a catalyst using hydrogen chloride and oxygen wherein the catalyst is an oxychlorination catalyst comprising (i) a carrier material, (ii) a palladium compound, a copper compound and a vanadium compound, and, optionally, (iii) an alkali earth metal compound.

2. A method according to claim 1 wherein the mole ratio of olefin or aromatic hydrocarbon:hydrogen chloride:oxygen is 1:0.1–10:0.05–5.

3. A method according to claim 1, wherein the catalyst is calcined in an oxygen-containing gas or in a nitrogen atmosphere at about 200° to about 700° C. before the oxychlorination reaction.

4. A method according to claim 1 wherein the palladium compound is at least one palladium compound selected from the group consisting of palladium halides (II), nitric acid salts of palladium (II), sulfuric acid salts of palladium (II), carboxylic acid salts of palladium (II), oxides of palladium (II), hydroxides of palladium (II), complexes of palladium, and double salts of these.

5. A method according to claim 1, wherein the palladium compound is at least one compound selected from the group consisting of $PdCl_2$, $PdBr_2$, $PdI_2$, $Pd(NO_3)_2$, $PdSO_4$, $Pd(O_2CCH_3)_2$, $Pd(O_2CC_2H_5)_2$, $Pd(O_2CC_3H_7)_2$, $PdO$, $Pd(OH)_2$, $Pd(NO_2)_2(NH_3)_2$, $[PD(NH_3)_4]Cl_2$, $PdCl_2(NH_3)_2$, $[Pd(NH_3)_4](NO_3)_2$, $Pd(CN)_2$, $K_2[Pd(CN)_4]$, $Pd(CN)_2(NH_3)_2$, $PdCl_2(CH_3CN)_2$, $PdCl_2(PhCN)_2$, $PdCl_2(1,5\text{-cyclooctadiene})$, $Pd(CH_3COCHCOCH_3)_2$, $PdCl_2[(PH)_3P]_2$, $(NH_4)_2[PdCl_6]$, $(NH_4)_2[PdCl_4]$, $K_2[PdCl_6]$, $K_2[PdCl_4]$, $K_2[Pd(NO_2)_4]$, $Na_2[PdCl_4]$, $Na_2[Pd(NO_2)_4]$ and $Pd[(PH)_3P]_4$.

6. A method according to claim 1 wherein the palladium compound is at least one compound selected from the group consisting of $Pd(O_2CCH_3)_2$, $Pd(O_2CC_2H_5)_2$, $Pd(O_2CC_3H_7)_2$ and $PdCl_2$.

7. A method according to claim 1 wherein the copper compound is at least one compound selected from the group consisting of salts, oxides and complexes of monovalent or bivalent copper.

8. A method according to claim 1, wherein the copper compound is at least one compound selected from the group consisting of $CuCl$, $CuCl_2$, $CuBr$, $CuBr_2CuI_2$, $Cu(NO_3)_2$, $CuSO_4$, $Cu_2(CN)_2$, $Cu(CN)_2$, $Cu(OH)_2$, $Cu_2P_2O_7$, $CuCO_3$, $2CuCO_3 Cu(OH)_2$, $CuO$, $Cu_2O$, $Cu(O_2CCH_3)_2$, $Cu(CH_3COCHCOCH_3)_2$, $[Cu(NH_3)_6]Cl_2$ and $[Cu(NH_3)_5]Cl_2$.

9. A method according to claim 1 wherein the copper compound is at least one compound selected from the group consisting of $CuCl_2$ and $Cu(NO_3)_2$.

10. A method according to claim 1 wherein the vanadium compound is at least one compound selected from the group consisting of salts and oxides of vanadium.

11. A method according to claim 1 wherein the vanadium compound is at least one compound selected from the group consisting of $V_2O_3$, $VO_2$, $V_2O_5$, $NH_4VO_3$, $Na_3VO_4$, $Na_4V_2O_7$, $VOCl_3$, $VCl_4$, $VCl_5$ and $VOSO_4$.

12. A method according to claim 1 wherein the vanadium compound is $V_2O_5$.

13. A method according to claim 1 wherein the carrier material is at least one member selected from the group consisting of $SiO_2$, $Al_2O_3$, $SiO_2\text{-}Al_2O_3$, $TiO_2$, $MgO$, $CaO$, $La_2O_3$, $CeO_2$, $SiO_2\text{-}TiO_2$, $SiC$, carbon, zeolite and clay minerals.

14. A method according to claim 1 wherein the carrier material is at least one member selected from the group consisting of $SiO_2$, $Al_2O_3$ and $TiO_2$.

15. A method according to claim 1 wherein, based on the carrier material, the amount of the palladium compound is about 0.01 to about 20% by weight calculated as palladium, and the amount of the copper compound is about 0.05 to about 40% by weight calculated as copper, and the amount of the vanadium compound is about 0.05 to about 40% by weight calculated as vanadium.

16. A method according to claim 1 which comprises, based on the carrier material, the amount of the palladium compound is about 0.1 to about 10% by weight calculated as palladium, and the amount of the copper compound is about 0.5 to about 20% by weight calculated as copper, and the amount of vanadium compound is about 0.5 to about 20% by weight calculated as vanadium.

17. A method according to claim 1 which further comprises an alkaline earth metal compound.

18. A method according to claim 17 wherein the alkaline earth metal compound is at least one compound selected from the group consisting of halides, nitric acid salts, sulfuric acid salts and carboxylic acid salts of alkaline earth metal, wherein the alkaline earth metal compound is selected from the group consisting of magnesium, calcium, strontium and barium.

19. A method according to claim 17, wherein the alkaline earth metal compound is at least one compound selected from the group consisting of $MgCl_2$, $MgBr_2$, $MgI_2$, $Mg(NO_3)_2$, $MgSO_4$, $Mg(O_2CCH_3)_2$, $Mg(O_2CC_2H_5)_2$, $Mg(O_2CC_6H_5)_2$, $Mg(O_2CH)_2$, magnesium phthalate, magnesium citrate, magnesium glycolate, $CaCl_2$, $CaBr_2$, $CaI_2$, $Ca(NO_3)_2$, $CaSO_4$, $Ca(O_2CCH_3)_2$, $Ca(O_2CC_2H_5)_2$, $Ca(O_2CC_6H_5)_2$, $Ca(O_2CH)_2$, calcium phthalate, calcium citrate, calcium glycolate, $SrCl_2$, $SrBr_2$, $SrI_2$, $Sr(NO_3)_2$, $SrSO_4$, $Sr(O_2CH)_2$, $BaCl_2$, $BaBr_2$, $BaI_2$, $Ba(NO_3)_2$, $BaSO_4$ and $Ba(O_2CH)_2$.

20. A method according to claim 17, wherein based on the carrier material, the alkaline earth metal compound is used in an amount of up to about 40% by weight calculated as alkaline earth metal.

* * * * *